(12) United States Patent
Bornea et al.

(10) Patent No.: US 9,792,549 B2
(45) Date of Patent: *Oct. 17, 2017

(54) EXTRACTION OF SEMANTIC RELATIONS USING DISTRIBUTIONAL RELATION DETECTION

(71) Applicant: International Business Machines Corporation, Armonk, NY (US)

(72) Inventors: Mihaela A. Bornea, White Plains, NY (US); James J. Fan, Mountain Lakes, NJ (US); Alfio M. Gliozzo, New York, NY (US); Christopher A. Welty, Flushing, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 350 days.

This patent is subject to a terminal disclaimer.

(21) Appl. No.: 14/549,577

(22) Filed: Nov. 21, 2014

(65) Prior Publication Data

US 2016/0148096 A1    May 26, 2016

(51) Int. Cl.
*G06N 5/02* (2006.01)
*G06N 99/00* (2010.01)
(Continued)

(52) U.S. Cl.
CPC ............. *G06N 5/02* (2013.01); *G06F 17/277* (2013.01); *G06F 17/30598* (2013.01);
(Continued)

(58) Field of Classification Search
CPC .... G06N 5/025; G06N 5/02; G06N 5/04; G06N 99/005; G06F 17/30598; G06F 17/30604; G06F 17/30702
(Continued)

(56) References Cited

U.S. PATENT DOCUMENTS 7,958,068 B2   6/2011   Smith et al.
8,200,656 B2   6/2012   Brown et al.
(Continued)

OTHER PUBLICATIONS

Bollegala D. et al., "Relational Duality: Unsupervised Extraction of Semantic Relations between Entities on the Web", WWW 2010, Apr. 26-30, 2010, Raleigh, North Carolina, USA.*
(Continued)

*Primary Examiner* — Dave Misir
(74) *Attorney, Agent, or Firm* — Cantor Colburn LLP; William Stock

(57) ABSTRACT

According to an aspect, a pair of related entities that includes a first entity and a second entity is received. Distributional relations are detected between the first entity and the second entity. The detecting includes identifying two sets of entities in a corpus, the first set including the first entity and at least one other entity that is semantically similar to the first entity, and the second set including the second entity and at least one other entity that is semantically similar to the second entity. Semantic relations are detected between entities in the first set and entities in the second set. A relation classifier is trained using the pair of related entities and detected semantic relations. The relation classifier model is applied to a new pair of entities to determine a likelihood of a semantic relation between the entities in the new pair of entities.

5 Claims, 7 Drawing Sheets

(51) Int. Cl.
G06F 17/30 (2006.01)
G06F 19/00 (2011.01)
G06F 17/27 (2006.01)

(52) U.S. Cl.
CPC .. *G06F 17/30604* (2013.01); *G06F 17/30702* (2013.01); *G06F 19/324* (2013.01); *G06N 5/022* (2013.01); *G06N 99/005* (2013.01)

(58) Field of Classification Search
USPC .......................................................... 706/55
See application file for complete search history.

(56) References Cited

U.S. PATENT DOCUMENTS

| | | | |
|---|---|---|---|
| 8,275,803 B2 | 9/2012 | Brown et al. | |
| 8,332,334 B2 | 12/2012 | Long et al. | |
| 2003/0004912 A1 | 1/2003 | Pant et al. | |
| 2008/0097951 A1* | 4/2008 | Gupta | G06N 5/025 706/59 |
| 2009/0019032 A1* | 1/2009 | Bundschus | G06F 19/3443 |
| 2009/0192954 A1* | 7/2009 | Katukuri | G06F 17/3061 706/11 |
| 2011/0125734 A1 | 5/2011 | Duboue et al. | |
| 2012/0077178 A1 | 3/2012 | Bagchi et al. | |
| 2012/0078062 A1 | 3/2012 | Bagchi et al. | |
| 2012/0301864 A1 | 11/2012 | Bagchi et al. | |
| 2013/0132308 A1 | 5/2013 | Boss et al. | |
| 2013/0246046 A1* | 9/2013 | Fan | G06F 17/2785 704/9 |
| 2014/0082003 A1* | 3/2014 | Feldman | G06F 17/30684 707/755 |
| 2015/0370782 A1* | 12/2015 | Fan | G06F 17/2785 704/9 |
| 2016/0148116 A1 | 5/2016 | Bornea et al. | |

OTHER PUBLICATIONS

Jonnalagadda S. et al., "Enhancing clinical concept extraction with distributional semantics", Journal of Biomedical Informatics, 45, pp. 129-140, Nov. 7, 2011.*

Nenriksson A. et al. "Identifying Synonymy between SNOMED Clinical Terms of Varying Length Using Distributional Analysis of Electronic Health Records", 2013.*

List of IBM Patents or Patent Applictions Treated as Related; (Appendix P), Filed Apr. 26, 2017, 2 pages.

* cited by examiner

EXTRACTION OF SEMANTIC RELATIONS USING DISTRIBUTIONAL RELATION DETECTION

BACKGROUND

The present disclosure relates generally to the extraction of semantic relations, and more specifically, to using distributional relation detection to extract semantic relations across documents in a corpus.

Much of human communication, whether it is in natural-language text, speech, and/or images, is unstructured. The semantics necessary to interpret unstructured information to solve problems is often implicit and is derived by using background information and inference. Unstructured data is contrasted with structured data, such as data in traditional database tables, where the data is well-defined, and the semantics are explicit. When structured data is used, queries are prepared to answer predetermined questions on the basis of necessary and sufficient knowledge of the meaning of the table headings (e.g., Name, Address, Item, Price, and Date). This is not the case with unstructured information where the semantics are not always explicit and it is often difficult to determine what an arbitrary string of text or an image really means.

With the enormous proliferation of electronic content on the web and within enterprises, unstructured information (e.g., text, images, and speech) is growing far faster than structured information. Whether it is general reference material, textbooks, journals, technical manuals, biographies, or blogs, this content contains high-value knowledge that is often important for informed decision making. The ability to leverage the knowledge latent in these large volumes of unstructured text lies in deeper natural-language analysis that can more directly infer answers to user questions.

Natural-language processing (NLP) techniques, which are also referred to as text analytics, infer the meaning of terms and phrases by analyzing their syntax, context, and usage patterns. Human language, however, is so complex, variable (there are many different ways to express the same meaning), and polysemous (the same word or phrase may mean many things in different contexts) that this presents an enormous technical challenge. Decades of research have led to many specialized techniques each operating on language at different levels and on different isolated aspects of the language understanding task. These techniques include, for example, shallow parsing, deep parsing, information extraction, word-sense disambiguation, latent semantic analysis, textual entailment, and co-reference resolution. None of these techniques is perfect or complete in their ability to decipher the intended meaning. Unlike programming languages, human languages are not formal mathematical constructs. Given the highly contextual and implicit nature of language, humans themselves often disagree about the intended meaning of any given expression.

Detecting semantic relations in text is very useful in both information retrieval and question answering because it enables knowledge bases (KBs) to be leveraged to score passages and retrieve candidate answers. Approaches for extracting semantic relations from text include rule-based methods that employ a number of linguistic rules to capture relation patterns. Other approaches include feature based methods that transform relation instances into a large amount of linguistic features such as lexical, syntactic and semantic features, and that capture the similarity between these features using vectors. Further approaches for extracting semantic relations include those that are kernel-based and focused on using tree kernels to learn parse tree structure related features.

SUMMARY

Embodiments include a system and computer program product for extraction of semantic relations using distributional relation detection. A method includes receiving, by a processor, a pair of related entities that includes a first entity and a second entity. Distributional relations are detected, by the processor, between the first entity and the second entity. The detecting includes identifying two sets of entities in a corpus. The first set of entities includes the first entity and at least one other entity that is semantically similar to the first entity. The second set of entities includes the second entity and at least one other entity that is semantically similar to the second entity. Semantic relations are detected between entities in the first set and entities in the second set. A relation classifier is trained using the pair of related entities and the detected semantic relations. The relation classifier model is applied, by the processor, to a new pair of entities to determine a likelihood of a semantic relation between the entities in the new pair of entities.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
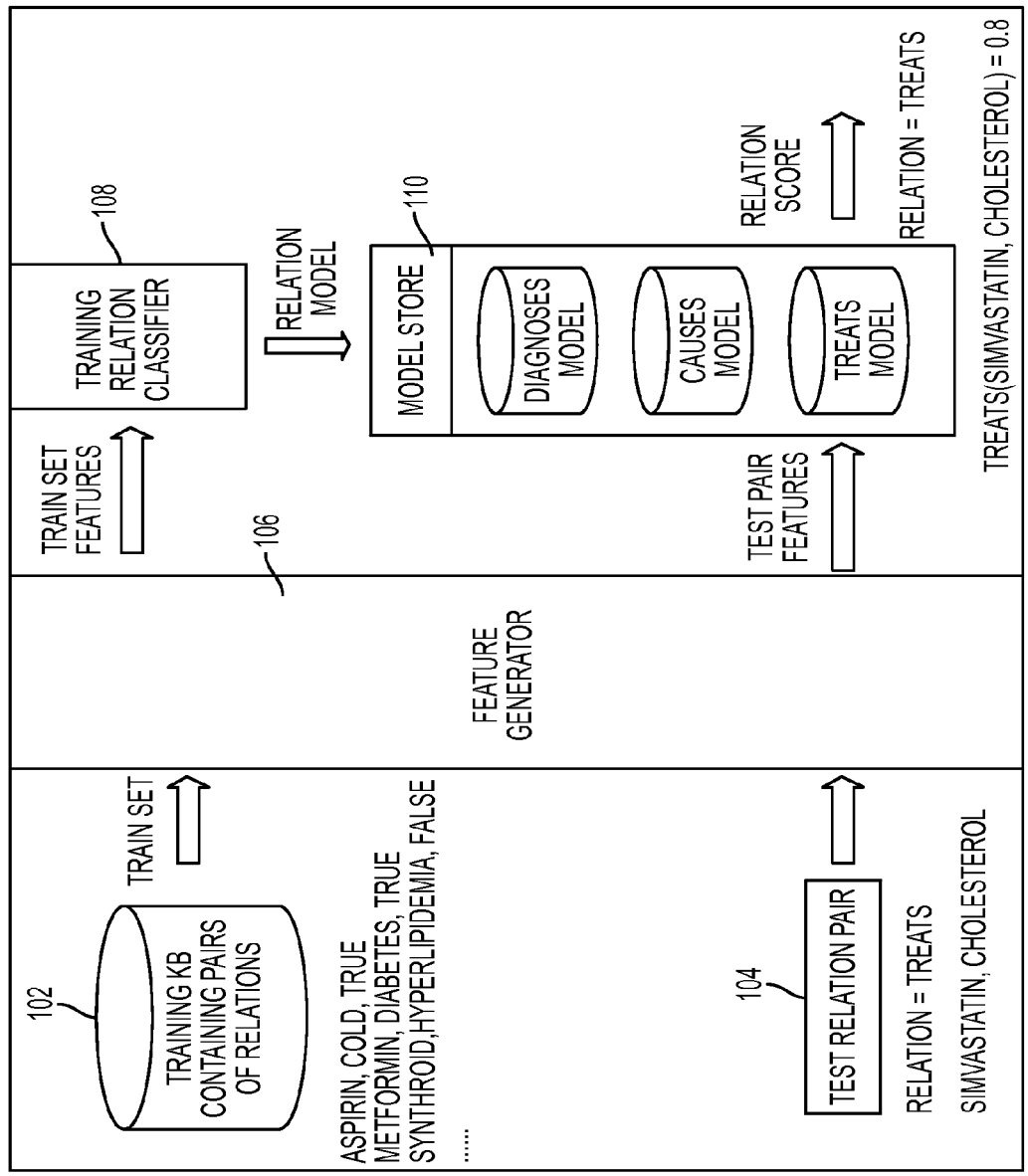
FIG. 1 depicts a block diagram of a process for performing distributional relation detection (DRD) in accordance with an embodiment.

Embodiments relate to a new methodology for relation detection, referred to herein as distributional relation detection (DRD) that can be used to identify relations between terms located in a corpus of documents even if the terms have never been mentioned in the same document. Embodiments of DRD can take into consideration the distributional properties of candidate pairs of terms and use those distributional properties as features to train a relation extraction algorithm. DRD can be trained by listing pairs of seed terms related by any given relation, and its coverage expanded to pairs of terms that never occurred together in the same document, thus allowing a substantial increase in coverage when compared to traditional relation extraction techniques. In addition, embodiments can be used to simplify relation extraction training procedures by avoiding the requirement of hand tagged training data showing the actual text fragment where the relation occurs. Thus, relation annotation is not required on documents, and the domain expert doing the annotating does not need to be skilled in natural language processing (NLP).

Many applications in the area of information extraction and NLP can benefit from understanding semantic relations between entities. As used herein, the terms "entity" and "term" are used interchangeably to refer to any meaningful linguistic expression that identifies an object of interest in the target domain. As used herein, the term "semantic relation" or "relation" refers to an association that exists between the meanings of two entities. A semantic relation can hold between two entities if they participate in a specific frame (e.g., medication prescribed for disease). Embodiments described herein can identify semantic relations and can use pre-existing semantic relations between entities as features for the machine learning algorithms described herein. Inherent challenges when tackling relation extraction can include a sparsity of data and a lack of resources. In contemporary automated relation extraction techniques, the meaning of a sentence where two entities are located is analyzed, and if that sentence explicitly expresses a relation, then the relation between the two entities is extracted. More recently, cross sentence relation extraction techniques have been introduced that require that the two entities to be in the same paragraph or document and these techniques rely on the document structure as an additional source of evidence. When using contemporary relation extraction techniques the two entities to be related must be mentioned in the same sentence or document, thus, preventing the ability to extract relations between entities located in different documents.

In contrast to contemporary relation extraction techniques that depend on the explicit occurrence of both entities in the same sentence or document, embodiments of DRD described herein can detect relations between entities across documents and thus, the use of DRD can result in a significantly increased coverage when compared to existing techniques. An embodiment of the DRD model is based on the distributional hypothesis, which suggests that semantically similar terms tend to occur in similar linguistic contexts. DRD can be used to find evidence from the contexts where entities have been found across a large corpus (e.g., a set of documents that can include unstructured text) and can use distributional similarity techniques to find similar information considering variants of the entities.

Embodiments described herein can be used to train supervised classifiers for each relation using features derived from unsupervised learning. For each relation, the training set can be composed of argument pairs for both positive and negative examples. In embodiments, the argument pairs are not limited to those found together in the same sentence or even the same document.

Examples related to the domain of the medical field are described herein, however embodiments are not limited to applications in the medical domain as embodiments can be applied to any domain that requires semantic relations to be extracted from text, including, but not limited to: the automotive domain (e.g., to facilitate automotive repairs), and a general question-answer (QA) system. When applied to a general QA system, embodiments can be utilized to detect relations between terms in candidate answers and questions.

Turning now to FIG. 1, a block diagram of a process for performing DRD in accordance with an embodiment is generally shown. As described previously, an embodiment of DRD is designed to detect semantic relations between terms in a corpus that occur within a sentence, across sentences (i.e., in two or more sentences) and across documents (i.e., in two or more documents).

An embodiment of DRD described herein can include a supervised learning technique that utilizes a training step. The supervised learning can include a training data set that contains positive and negative examples of pairs of terms annotated with a given set of relations (e.g. diagnoses, causes, treats). Features describing the pairs of entities can be obtained using data in an ontology and distributional semantics (DS). The training knowledgebase (KB) 102 shown in FIG. 1 contains entity pairs of relations and a binary assessment of whether the entities are related by the relation ("true") or are not related ("false"). An example "Treats" relation training set shown in FIG. 1 includes: Aspirin, Cold, true; Metformin, Diabetes, true; and "Synthroid, Hyperlipidemia, false. During the training phase, a model can be built for each of the given relations. The training phase can include inputting a training set from the training KB 102 into a feature generator 106 which outputs training set features. The training set features are then input to a training relation classifier 108 which creates one or more relation classifier models (e.g., one relation classifier model for each relation in the domain) that are stored in the model store 110. In an embodiment there is a different training relation classifier 108 for each of the relations in the domain. In another embodiment, two or more relations in the domain share a training relation classifier 108. The model store 110 shown in FIG. 1 includes a separate relation classifier model for each relation (e.g., diagnoses, causes, and treats).

After the training phase is completed, the system can be used for relation detection by applying the desired relation classifier model in the model store 110 to a new pair of entities (e.g., a pair of terms). As shown in FIG. 1, the test relation pair 104 is input to the feature generator 106 which outputs test pair features. The test pair features are then input to the model store 110 which outputs a relation score that can indicate the probability that a particular semantic relation applies for the input terms. In the example shown in FIG. 1, the test pair of terms is Simvastatin, Cholesterol and the relation score produced by the system for the "Treats" relation is 0.8. This indicates that there is an 80% chance that Simvastatin treats Cholesterol.

In an embodiment, the training relation classifier 108 is used only in the training phase. The training relation classifier 108 can use the relation examples in the training KB 102 together with the features that are generated by the feature generator 106 to train a logistic classifier model, or relation classifier model, for each relation of interest in the domain. In an embodiment, a relation classifier model is trained for each relation to be detected using, for example, a linear regression classifier. For each relation, both positive and negative examples are utilized, with each example having a set of features. Once the relation classifier models are trained by the training relation classifier 108 and the corresponding relation classifier models are stored in the model store 110, a new pair of terms referred to as the test relation pair 104, can be input to the feature generator 106. The feature generator 106 generates test pair features which are then input to a relation classifier model in model store 110. The relation classifier model classifies the relation and outputs a score predicting the existence of a particular relation (e.g., selected from a relation corresponding to one of the relation classifier models) between the terms in the test relation pair 104. As described herein, the model store 110 can contain relation classifier models for each relation, be populated during the training phase by the training relation classifier 108, and be used at test/run-time for detecting relations between argument pairs The feature generator 106 can be used to extract features that describe pairs of entities based on information learned from text (such as that stored in the LSA database 210 and the DS database 212 shown in FIG. 2) and information stored in a domain ontology 202 (such as the Unified Medical Language System or "UMLS" for the medical domain). The feature generator 106 shown in FIG. 1 can be used during all of the training, test, and run-time phases to create features which describe pairs of entities. As used herein, the term "training phase" refers to applying the algorithms needed for building the relation classifier models and the terms "test phase" and "run-time phase" refer to applying the learned relation classifier models built during the training phase to new data. During the training phase, the feature generator 106 can produce sets of features for all or a subset of the entity pairs of relations in the training KB 102. This is contrasted with the test phase, where the feature generator 106 can produce features for entities in a test relation pair 104.

Figure 2:
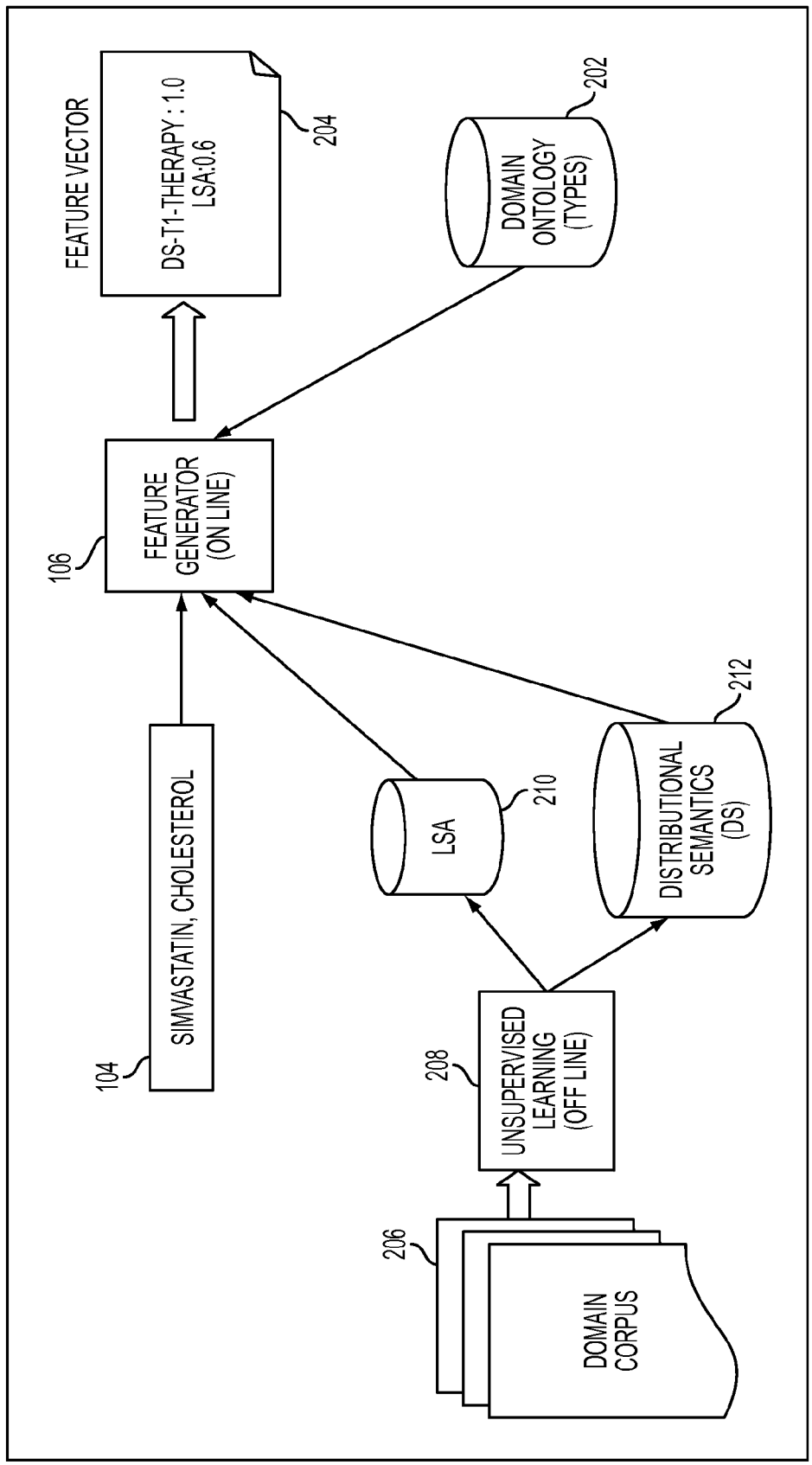
FIG. 2 depicts a block diagram of a dataflow for feature generation in accordance with an embodiment.

Turning now to FIG. 2, a block diagram of a dataflow of the feature generator 106 is generally shown in accordance with an embodiment. The dataflow shown in FIG. 2 can be used by embodiments for extracting features that describe a pair of entities (or terms) that are input to the feature generator 106. As shown in FIG. 2, a corpus containing content related to a particular domain, or a domain corpus 206, is used as input to an unsupervised learning process 208 which can be performed in an offline mode. As used herein, the term "offline mode" refers to processing that generally only happens only one time and as input to another phase. In an embodiment, the results of the unsupervised learning process 208 are available before starting the training phase and used as input to the training phase.

In an embodiment, the unsupervised learning process 208 includes performing DS to determine entity types and semantic contexts containing both entities. Features that include argument types can be derived from text (e.g., from the domain corpus 206) using DS. In a QA application, where a relation pair includes a question term and a candidate answer term, these argument types can include: typing for candidate answer and question term; syntactic connections in text between candidate answer and question term; similar terms expansion for candidate answer and question term; and argument connection across sentence using similar term expansion. Syntactic connections can also be made between arguments in the corpus, these can often include connections that are of high precision and low recall (e.g., explicit mention of the relations found in text (Simvastatin treats hyperlipidemia), dependencies such as nnModification_modifiernoun.)

Syntactic connections between terms similar to the arguments in the domain corpus 206 can also be derived, and these can often include connections that are of high recall and low precision. For example, given the two terms simvastatin and hyperlipidemia, types can be derived from domain corpus 206 by applying "is a" patterns that can be assigned to each type. This can result in simvastatin having types of medication, treatment, inhibitor, therapy, agent, dose, and drug. In an embodiment a reliability indicator can also be associated with each time. Applying "is a" patterns to the term hyperlipidemia can result, for example, in the types of cause, disorder, condition, diabetes, syndrome, resistance, risk factor, factor, disease, and symptom. These types can be stored in the DS database 212.

The unsupervised learning 208 can also detect relations in the domain corpus 206 that are not found in the same document. For example, suppose that in the domain corpus 206 no connection is found between the terms simvastatin and hyperlipidemia, that is these terms are not found in the same sentence or document. This lack of connection can be due to the sparsity of terms in the domain corpus 206. In an embodiment, one or both of these terms is not found in the domain corpus.

Figure 3:
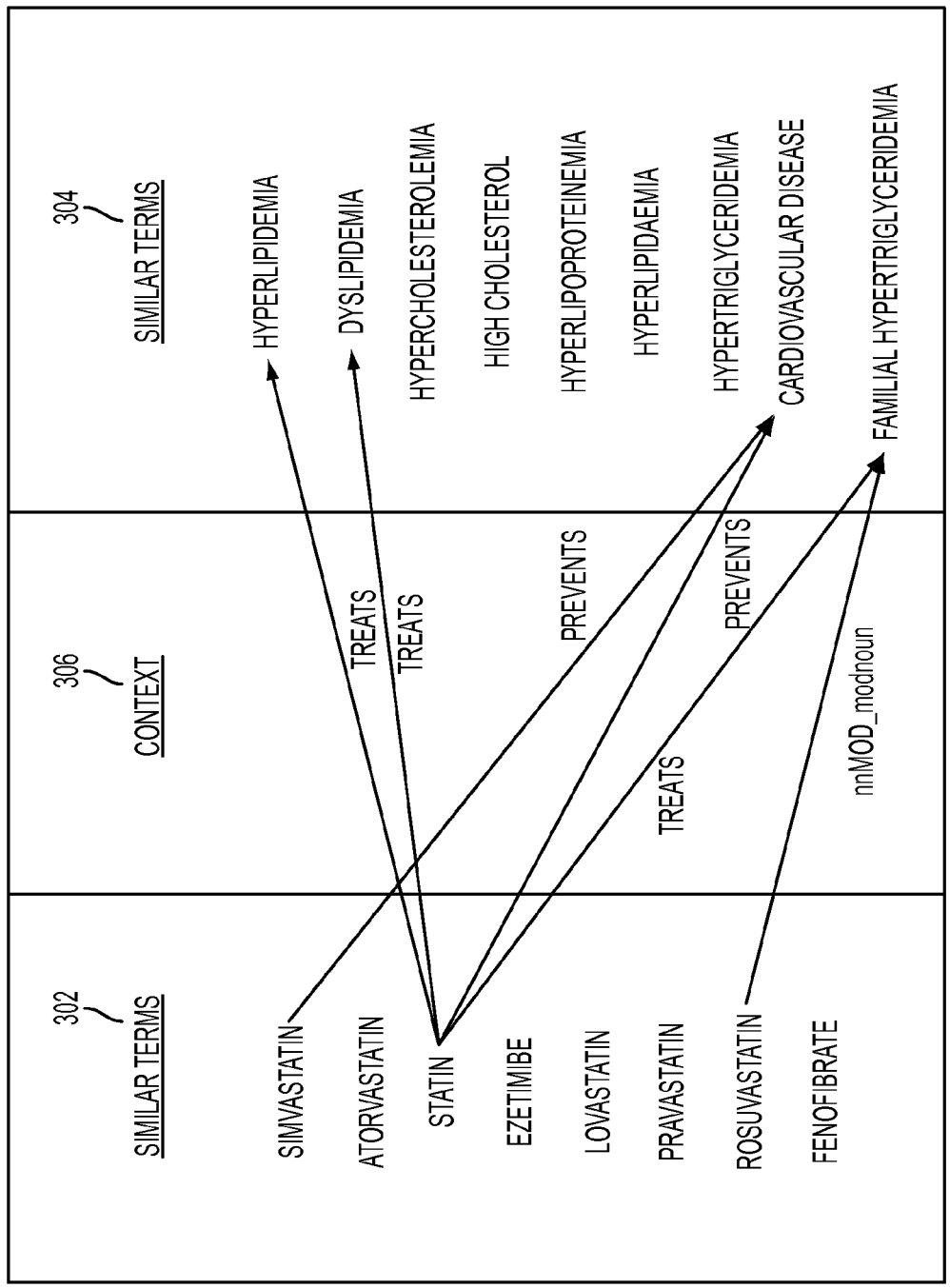
FIG. 3 depicts an example of additional relations that can be found by performing DRD in accordance with an embodiment.

Turning now to FIG. 3, an example of additional relations that can be found between simvastatin and hyperlipidemia by performing DRD are generally shown in accordance with an embodiment. As shown in FIG. 3, a determination can be made that simvastatin is semantically similar to atorvastatin, statin, ezetimibe, lovastatin, pravastatin, rosuvastatin, and fenofibrate. In addition, it can be determined that hyperlipidemia is semantically similar to dyslipidemia, hypercholesterolemia, high cholesterol, hyperlipoproteinemia, hyperlipidaemia, hypertriglyceridemia, cardiovascular disease, and familial hypertriglyceridemia. In an exemplary embodiment, the open source framework JoBim Text is used to acquire the semantically similar terms. Embodiments are not limited to the use of JoBim Text as any other corpus based or dictionary based technique to asses substitutability between terms can be used to acquire similar terms. Connections between these similar terms in common contexts can be used to detect relations between simvastatin and hyperlipidemia. In an embodiment, the DS term contexts can include the paths between terms. The similar terms are used as arguments to improve relation coverage. For example, since statin treats hyperlipidemia and because statin is similar to simvastatin, then it can be determined, using DRD, that simvastatin treats hyperlipidemia. In this manner, the treat relation is detected through the common context of similar terms.

As shown in the FIG. 3, the "treats" relation between simvastatin and hyperlipidemia can be given a weight of three since there are three connections between similar terms in the context of treat: statin and hyperlipidemia; statin and dyslipidemia; and statin and familial hypertriglyceridemia. Also as shown in FIG. 3, the "prevents" relation can be given a weight of two since there are two connections between similar terms in the context of prevents: simvastatin and cardiovascular disease; and statin and familial hypertriglyceridemia. Finally, as shown in FIG. 3, the "nnMod-modnoun" relation can be given a weight of one since there is one connection between similar terms in the context of nnMod-modnoun: rosuvastatin and familial hypertriglyceridemia.

In an embodiment, only a threshold number of relevant similar terms are considered for the additional relational detection shown in FIG. 3. This threshold can reflect a measurement of similarity (e.g., a likelihood) between a term and a candidate similar term.

Referring back to FIG. 2, additional features can include those that are derived using latent semantic analysis (LSA) which can be performed to determine a similarity between the terms. In an embodiment, a candidate answer and question term are similar if they co-occur in similar documents.

Both the LSA database 210 and the DS database 212, as well as a domain ontology 202 can be used as input to the feature generator 106 to generate a feature vector 204. Two examples of the feature vector 204 are shown in FIG. 1, the feature vector 204 is labeled in FIG. 1 as "train set features" (shown being input to the training relation classifier) and it as "test pair features" (shown being input to the model store 110). For embodiments directed to the medical area, the domain ontology 202 can be the Unified Medical Language System (UMLS) which can be used by the feature generator 106 to extract semantics types and groups.

A domain ontology 202, such as the UMLS, can have different granularity of types: a fine granularity, a medium granularity, and a coarse granularity. For an example entity pair that includes simvastatin and hyperlipidemia, where the UMLS is used as the domain ontology 202, a fine granularity of a type can include the medical subject heading (MSH) taxonomy. An example of a fine granularity type for this entity pair is the "is a" relation for each argument, which will become features, resulting in types that indicate, for example, that cholesterol inhibitors (coded as C0003277 in UMLS) are a super type of simvastatin and that dyslipidemias (coded as C0242339 in UMLS) are a super type of hyperlipidemia. An example of a medium granularity type derived from the UMLS is a semantic type, such as simvastatin is a pharmacological substance (coded in UMLS as T121) and hyperlipidemia is a disease or syndrome (code in UMLS as T047). An example of a coarse granularity type derived from the UMLS is a semantic group, such as simvastatin is a chemical (coded in UMLS as CHEM) and hyperlipidemia is a disorder (coded in UMLS as DISO). In this example, only a single type is extracted from the UMLS for each entity, however embodiments support multiple codes being extracted for each entity/granularity combination. For example, simvastatin can be classified as having two or more medium granularity types including pharmacological substance (coded in UMLS as T121 and organic chemical (coded in UMLS as T109). The feature generator 106 can be used to extract features that describe pairs of entities based on information learned from text (such as that stored in the LSA database 210 and the DS database 212) and information stored in a domain ontology 202 (such as the UMLS for the medical domain).

Figure 4:
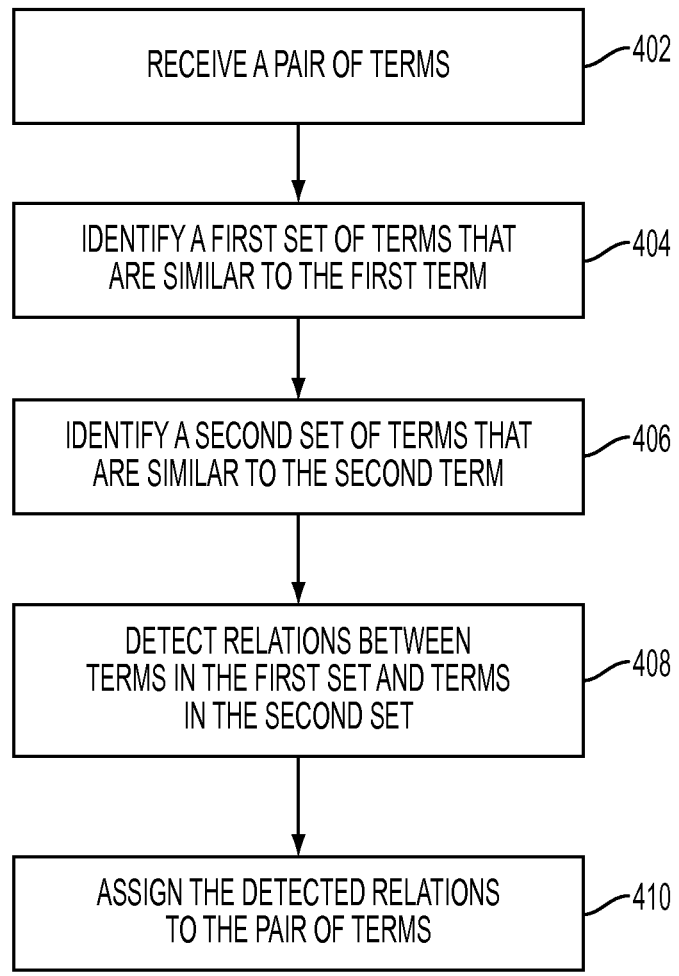
FIG. 4 depicts a process flow for detecting additional relations in accordance with an embodiment.

Turning now to FIG. 4, a process for performing DRD is generally shown in accordance with an embodiment. At block 402, a pair of terms (entities) that includes a first term and a second term is received. At block 404, a first set of terms that are semantically similar to the first term are identified, and at block 406 a second set of terms that are semantically similar to the second term are identified. As used herein, the term "semantically similar" refers to the fact that the similar terms can be substituted in context while preserving the original meaning of the sentence. For example, in the sentence "He was infected by a virus", the word "virus" is semantically similar to and can be substituted with the word "bacteria" without changing the meaning of the sentence. Thus, the sentences "He was infected by a virus" and "He was infected by a bacteria" have the same meaning. Relations are detected between terms in the first set and terms in the second set at block 408. At block 410, the detected relations are assigned to the pair of terms. In an embodiment, only those detected relations that occur more than a specified number of times are output as part of the feature vector 204. In the example shown in FIG. 3, if the specified number is two, then only the treats and prevents relation is output since they both occur two or more times. In another embodiment, only a specified number of detected relations (i.e., those occurring most often) are output as part of the feature vector. In the example shown in FIG. 3, if the specified number of detected relations is three (or more), then all three detected relations are output.

Figure 5:
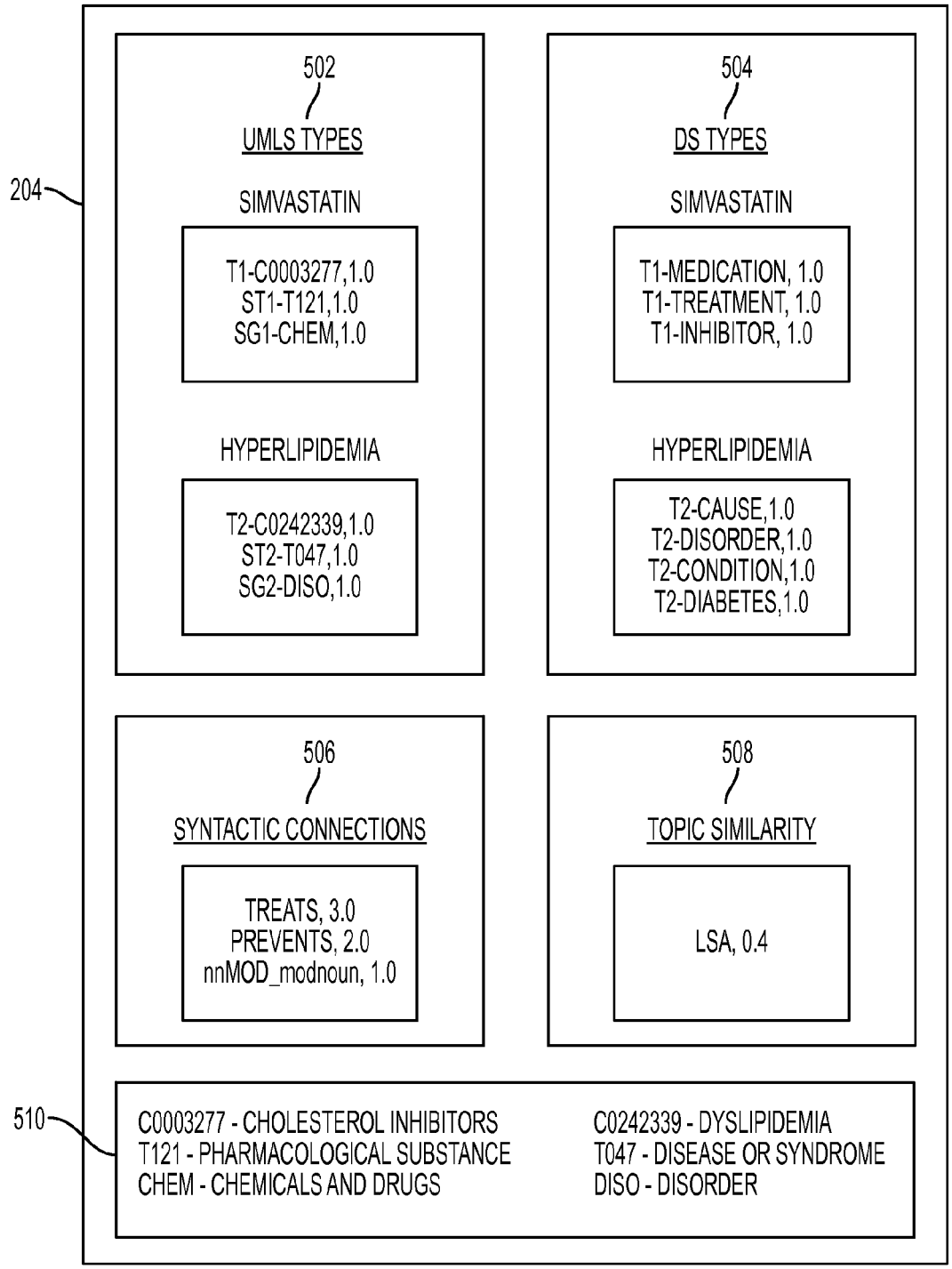
FIG. 5 depicts an example of a feature vector that can be generated for the example shown in FIG. 3 in accordance with an embodiment.

FIG. 5 depicts an example of a feature vector 204 that can be generated by the feature generator 106 for the example shown in FIG. 3 in accordance with an embodiment. In an embodiment, the feature vector 204 is output from the feature generator 106 and input to the training relation classifier 108 or the model store 110 shown in FIG. 1. The feature vector 204 shown in FIG. 5 includes UMLS types 502 for both terms with the UMLS unique identifier definitions 510 at the bottom of FIG. 5. For the first argument, simvastatin, T1-00003277 (with label Cholesterol Inhibitors) is the MSH type, ST1-T121 (with label Pharmacological Substance) is the semantic type and SG1-CHEM (with label Chemicals and Drugs) is the semantic group. As shown in the example in FIG. 5, each UMLS derived feature can be assigned a weight of 1.0 indicating a highest degree of reliability. Also shown in FIG. 5 are the DS derived types 504 for each term, and in the example shown in FIG. 5 each is also assigned a weight of 1.0. The feature vector 204 also includes the syntactic connections 506 between arguments as described previously in reference to FIG. 3, with each syntactic connection feature receives a weight equal to its frequency among the expansions of the arguments. The weight for the LSA feature for the example shown in FIG. 5 is the LSA similarity score of 0.4.

An embodiment can utilize JoBimText, which is an example of framework for DS, to aid in generating contents of the feature vector. JoBimText includes an open source framework for DS that uses lexicalized features for automatic text expansion using contextualized distributional similarity. In an embodiment, the domain corpus 206 is input to the JoBimText framework and preprocessing operation is run to identify terms and their relations. After preprocessing is complete, a distributional thesaurus (DT) that represents words by means of cluster of other distributional similar words that can be regarded as near synonyms can be acquired from the JoBimText framework.

For embodiments utilized in the medical domain, a domain specific JoBimText annotator can be created using a dependency parser adapted for the medical domain and a relation extraction system able to identify UMLS relations in text. A role of the relation extraction system can be to provide additional constraints to the way word contexts are described, allowing the capture of dependencies between relation arguments that otherwise might not be allowed using only the parser. In addition, domain specific terms can be mapped into their corresponding UMLS identifiers (e.g., CUIs). Knowing CUIs for each term can make it possible to get their corresponding types and other relevant information from the domain ontology 202.

In an embodiment, similar term expansion can be performed using the JoBimText framework. In particular, the JoBimText framework can be utilized to expand each relation argument to its distributionally similar terms in order for the syntactic connections to be detected between terms similar to the arguments in the corpus. The feature set can be expanded to the syntactic connections between the k most similar terms of the first argument and the first k similar terms of the second argument. Using similar term expansion to produce features can allow a relation detection mechanism that exceeds the limit of the sentence. Distributionally similar terms can appear in multiple sentences and in multiple documents across the corpus. This feature increases significantly the recall.

Figure 6:
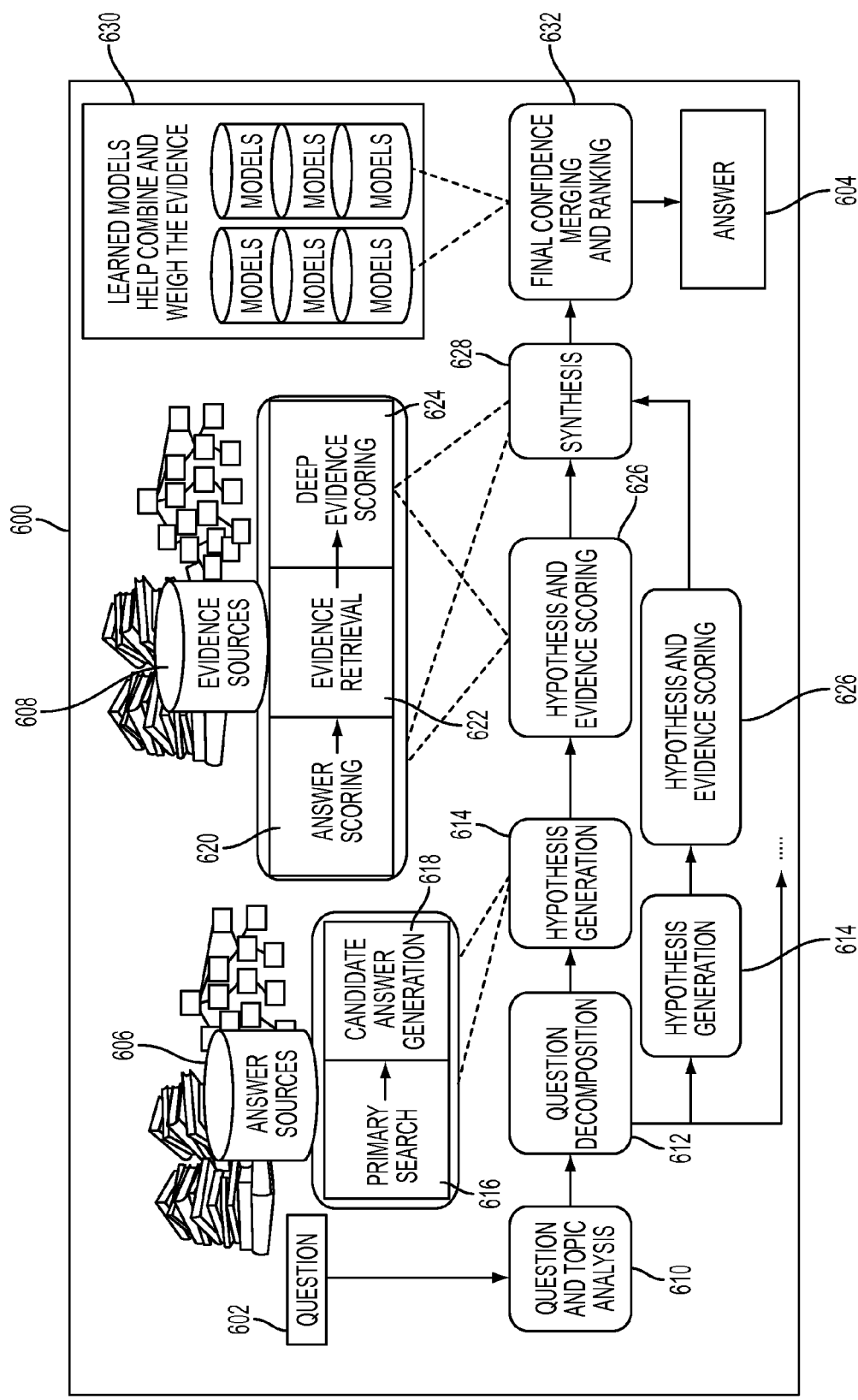
FIG. 6 depicts a high-level block diagram of a question-answer (QA) framework where embodiments of DRD can be implemented in accordance with an embodiment.

Turning now to FIG. 6, a high-level block diagram of a question-answer (QA) framework 600 where embodiments described herein can be utilized is generally shown.

The QA framework 600 can be implemented to generate an answer 604 (and a confidence level associated with the answer) to a given question 602. In an embodiment, general principles implemented by the framework 600 to generate answers 604 to questions 602 include massive parallelism, the use of many experts, pervasive confidence estimation, and the integration of shallow and deep knowledge. In an embodiment, the QA framework 600 shown in FIG. 6 is implemented by the Watson™ product from IBM.

The QA framework 600 shown in FIG. 6 defines various stages of analysis in a processing pipeline. In an embodiment, each stage admits multiple implementations that can produce alternative results. At each stage, alternatives can be independently pursued as part of a massively parallel computation. Embodiments of the framework 600 don't assume that any component perfectly understands the question 602 and can just look up the right answer 604 in a database. Rather, many candidate answers can be proposed by searching many different resources, on the basis of different interpretations of the question (e.g., based on a category of the question.) A commitment to any one answer is deferred while more and more evidence is gathered and analyzed for each answer and each alternative path through the system.

As shown in FIG. 6, the question and topic analysis 610 is performed and used in question decomposition 612. Hypotheses are generated by the hypothesis generation block 614 which uses input from the question decomposition 612, as well data obtained via a primary search 616 through the answer sources 606 and candidate answer generation 618 to generate several hypotheses. Hypothesis and evidence scoring 626 is then performed for each hypothesis using evidence sources 608 and can include answer scoring 620, evidence retrieval 622 and deep evidence scoring 624.

A synthesis 628 is performed of the results of the multiple hypothesis and evidence scorings 626. Input to the synthesis 628 can include answer scoring 620, evidence retrieval 622, and deep evidence scoring 624. Learned models 630 can then be applied to the results of the synthesis 628 to generate a final confidence merging and ranking 632. An answer 604 (and a confidence level associated with the answer) is then output.

Relation extraction plays a key role in information extraction in the QA framework 600 shown in FIG. 6. Embodiments of DRD disclosed herein can be utilized by the QA framework 600 to improve relation extraction and to expand it to cover relations between terms that are in different documents. Embodiments can be used, for example, by the answer scoring 620, deep evidence scoring 624, and candidate answer generation 618.

The framework 600 shown in FIG. 6 can utilize embodiments of the training data collection and the model training described herein to create learned models 630 by training statistical machine learning algorithms on prior sets of questions and answers to learn how best to weight each of the hundreds of features relative to one another. These weights can be used at run time to balance all of the features when combining the final scores for candidate answers to new questions 602. In addition, embodiments can be used to generate a KB based on a corpus of data that replaces or supplements commercially available KBs.

Figure 7:
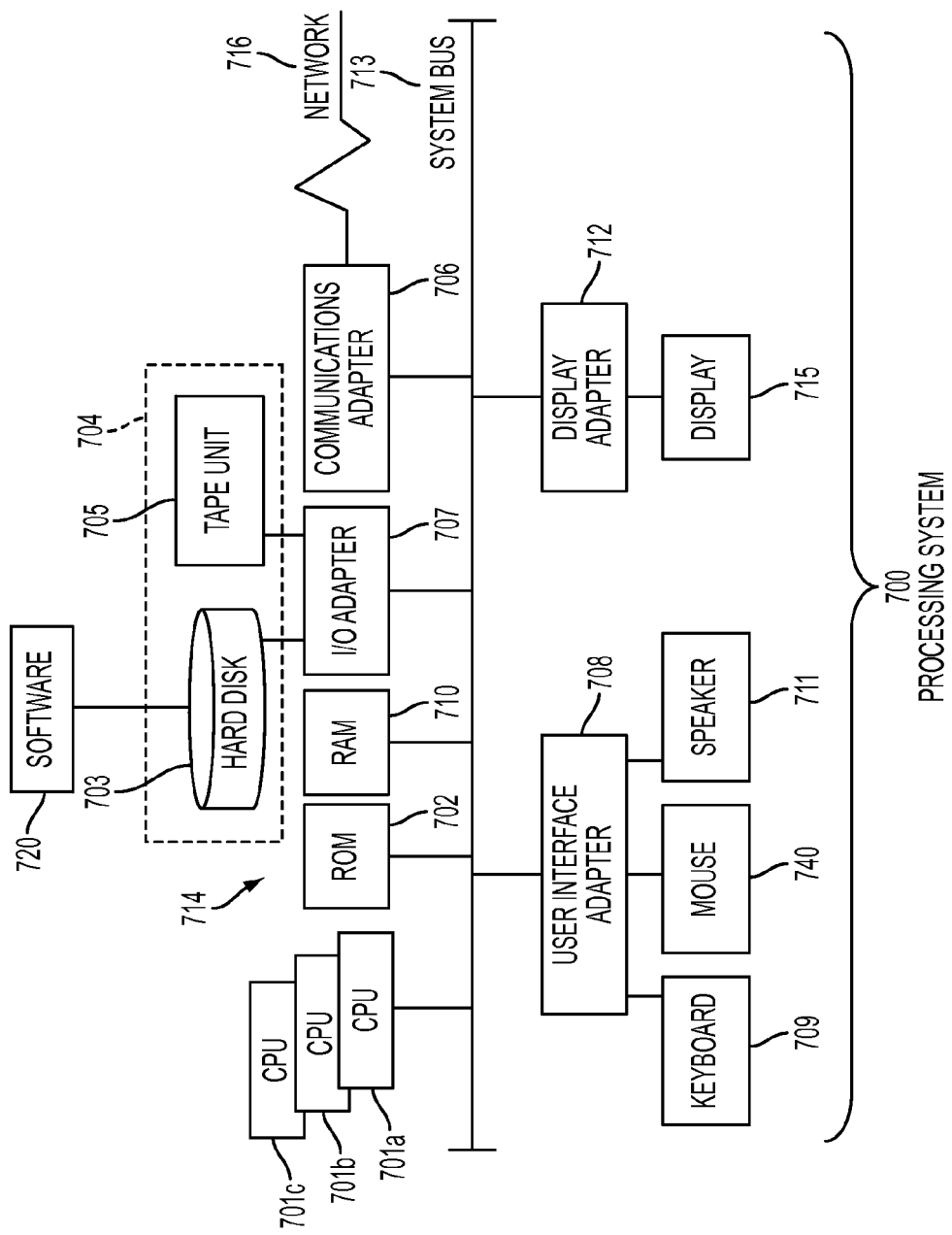
FIG. 7 depicts a processing system for DRD in accordance with an embodiment.

Referring now to FIG. 7, there is shown an embodiment of a processing system 700 for implementing the teachings herein. In this embodiment, the processing system 700 has one or more central processing units (processors) 701a, 701b, 701c, etc. (collectively or generically referred to as processor(s) 701). Processors 701 are coupled to system memory 714 and various other components via a system bus 713. Read only memory (ROM) 702 is coupled to system bus 713 and may include a basic input/output system (BIOS), which controls certain basic functions of the processing system 700. The system memory 714 can include ROM 702 and random access memory (RAM) 710, which is read-write memory coupled to system bus 713 for use by processors 701.

FIG. 7 further depicts an input/output (I/O) adapter 707 and a network adapter 706 coupled to the system bus 713. I/O adapter 707 may be a small computer system interface (SCSI) adapter that communicates with a hard disk 703 and/or tape storage drive 705 or any other similar component. I/O adapter 707, hard disk 703, and tape storage drive 705 are collectively referred to herein as mass storage 704. Software 720 for execution on processing system 700 may be stored in mass storage 704. The mass storage 704 is an example of a tangible storage medium readable by the processors 701, where the software 720 is stored as instructions for execution by the processors 701 to perform a method, such as the process flows of FIGS. 1-2 and 4. Network adapter 706 interconnects system bus 713 with an outside network 716 enabling processing system 700 to communicate with other such systems. A screen (e.g., a display monitor) 715 is connected to system bus 713 by display adapter 712, which may include a graphics controller to improve the performance of graphics intensive applications and a video controller. In one embodiment, adapters 707, 706, and 712 may be connected to one or more I/O buses that are connected to system bus 713 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 713 via user interface adapter 708 and display adapter 712. A keyboard 709, mouse 740, and speaker 711 can be interconnected to system bus 713 via user interface adapter 708, which may include, for example, a Super I/O chip integrating multiple device adapters into a single integrated circuit.

Thus, as configured in FIG. 7, processing system 700 includes processing capability in the form of processors 701, and, storage capability including system memory 714 and mass storage 704, input means such as keyboard 709 and mouse 740, and output capability including speaker 711 and display 715. In one embodiment, a portion of system memory 714 and mass storage 704 collectively store an operating system such as the AIX® operating system from IBM Corporation to coordinate the functions of the various components shown in FIG. 7.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer program product comprising:
   a tangible storage medium readable by a processing circuit and storing instructions for execution by the processing circuit to perform a method comprising:
   receiving a pair of entities that includes a first entity and a second entity the first entity located in a first document and not located in a second document, and the second entity located in the second document and not located in the first document;
   detecting distributional relations between the first entity and the second entity, the detecting including:
   identifying two sets of entities in a corpus, the first set including the first entity and at least one other entity that is semantically similar to the first entity, and the second set including the second entity and at least one other entity that is semantically similar to the second entity;
   detecting semantic relations between entities in the first set and entities in the second set; and
   assigning at least a subset of the detected semantic relations, based on the number of times that the semantic relations are detected between the entities in the first set and the entities in the second set, to the received pair of entities;
   training a relation classifier model in a training phase with a training data set that includes features describing the received pair of entities and the assigned semantic relations, wherein the training phase includes inputting the training data set from a training knowledge base into a feature generator that outputs the features for the training data set, and the features are then input to a training relation classifier which creates the relation classifier model; and
   applying the relation classifier model to a new pair of entities to determine a likelihood of a semantic relation between entities in the new pair of entities.

2. The computer program product of claim 1, wherein the training a relation classifier model includes supervised training.

3. The computer program product of claim 1, wherein the assigned semantic relations are used as features to train the relation classifier model.

4. The computer program product of claim 1, wherein the identifying is based on distributional semantics.

5. A system comprising:
   a memory having computer readable computer instructions; and
   a processor for executing the computer readable instructions, the computer readable instructions including:
   receiving a pair of entities that includes a first entity and a second entity the first entity located in a first document and not located in a second document, and the second entity located in the second document and not located in the first document;
   detecting distributional relations between the first entity and the second entity, the detecting including:
   identifying two sets of entities in a corpus, the first set including the first entity and at least one other entity that is semantically similar to the first entity, and the second set including the second entity and at least one other entity that is semantically similar to the second entity;
   detecting semantic relations between entities in the first set and entities in the second set; and
   assigning at least a subset of the detected semantic relations, based on the number of times that the semantic relations are detected between the entities in the first set and the entities in the second set, to the received pair of entities;
   training a relation classifier model in a training phase with a training data set that includes features describing the received pair of related entities and the assigned semantic relations, wherein the training phase includes inputting the training data set from a training knowledge base into a feature generator that outputs the features for the training data set, and the features are then input to a training relation classifier which creates the relation classifier model; and
   applying the relation classifier model to a new pair of entities to determine a likelihood of a semantic relation between entities in the new pair of entities.

* * * * *